US00PP11481P

United States Patent [19]

Guidry

[11] Patent Number: Plant 11,481

[45] Date of Patent: Aug. 15, 2000

[54] AZALEA PLANT NAMED 'SWEET LORRAINE'

[76] Inventor: Guy Joseph Guidry, 88 N. Magnolia Dr., Covington, La. 70433

[21] Appl. No.: 08/907,472

[22] Filed: Aug. 8, 1997

[51] Int. Cl.[7] ..... A01H 5/00

[52] U.S. Cl. ..... Plt./239

[58] Field of Search ..... Plt./55, 56, 238, Plt./239

[56] References Cited

U.S. PATENT DOCUMENTS

| | | | |
|---|---|---|---|
| P.P. 2,490 | 4/1965 | Sakiyama | Plt./56 |
| P.P. 10,437 | 6/1998 | Glaser | Plt./57 |
| P.P. 10,438 | 6/1998 | Lee | Plt./57 |

*Primary Examiner*—Howard J. Locker
*Assistant Examiner*—Kent L. Bell

[57] ABSTRACT

A new and distinct variety of Azalea plant named 'Sweet Lorraine' particularly characterized by its unique small leaves, its very tight internode space, and a compact, dense, and vigorous growth habit.

3 Drawing Sheets

BACKGROUND OF THE INVENTION

This invention relates to the discovery of a new and distinct variety of evergreen azalea plant named 'Sweet Lorraine' which was discovered by me as a naturally occurring branch sport of an azalea plant named 'Wakaebisu' (unpatented), a known cultivar of the genus Rhododendron and of the indicum species, also known as a Satsuki variety.

At the time of my discovery referred to above, I was growing in my nursery, located in Metairie, La., an azalea named 'Wakaebisu'. In the course of my care and cultivation of this plant, my attention was attracted to a branch that was substantially different from the rest of the plant. This branch was taken and used as a cutting and had the following qualities. The leaf size was significantly smaller, being ½ to ¼ the size of the parent. The internodal space was significantly shorter than the parent. From the subsequent measurements I took, I determined that the average internode was ⅛ of an inch, which is four times less than the natural internode of the parent. As a result, the foliage is more dense. The sport also had a very unique growth habit that resembled a witches broom. Continued study and observation of the discovered sport and its progeny showed that during the growing season vegetative buds form and swell, resembling juvenile flower buds. Upon opening, branches break very rapidly from the terminal buds and subsequently and sporadically from axillary buds (without pruning). Sporadic and frequent growth (resembling a witches broom) rapidly develops into desirable branching with miniature foliage. The result of this unique growth habit is a plant which is more characteristic of a mature plant exhibiting an aged appearance. Flowers of the new plant are identical in shape and color to the parent, although it does occasionally produce smaller blooms (about 1½ inches) than the parent's typical 2–2½ inch blooms. This appears to be the result of the competition within the system from the unusual number of flower buds. This quality allows for the new plant to have an abundance of flowers that more fully cover the plant, than the parent.

Asexual propagation by cuttings over several generations performed by me at my nursery located in Metairie, La., (and in Covington, La.) proved that the unique characteristics of 'Sweet Lorraine' as stated within, which distinguishes it from its parent and other varieties known to me, are new and distinct, fixed and true and can be reproduced.

The ultimate size is unknown, as no plant has yet reached maturity. Three year old plants have reached heights of 27 inches with a width of 23 inches. Because this new variety has miniature foliage, a dense growth habit, and excessive branching that forms quickly due to its qualities, it is an excellent new plant for the bonsai market. 'Sweet Lorraine' can be trained to any tree form (or grown as a shrub). With pruning, the foliage becomes even smaller and extremely dense in a short time frame. This new plant has a general attractiveness particularly suited for the bonsai market and extremely desirable for the commercial market as well.

BRIEF DESCRIPTION OF THE PHOTOGRAPHS

Figure 1:
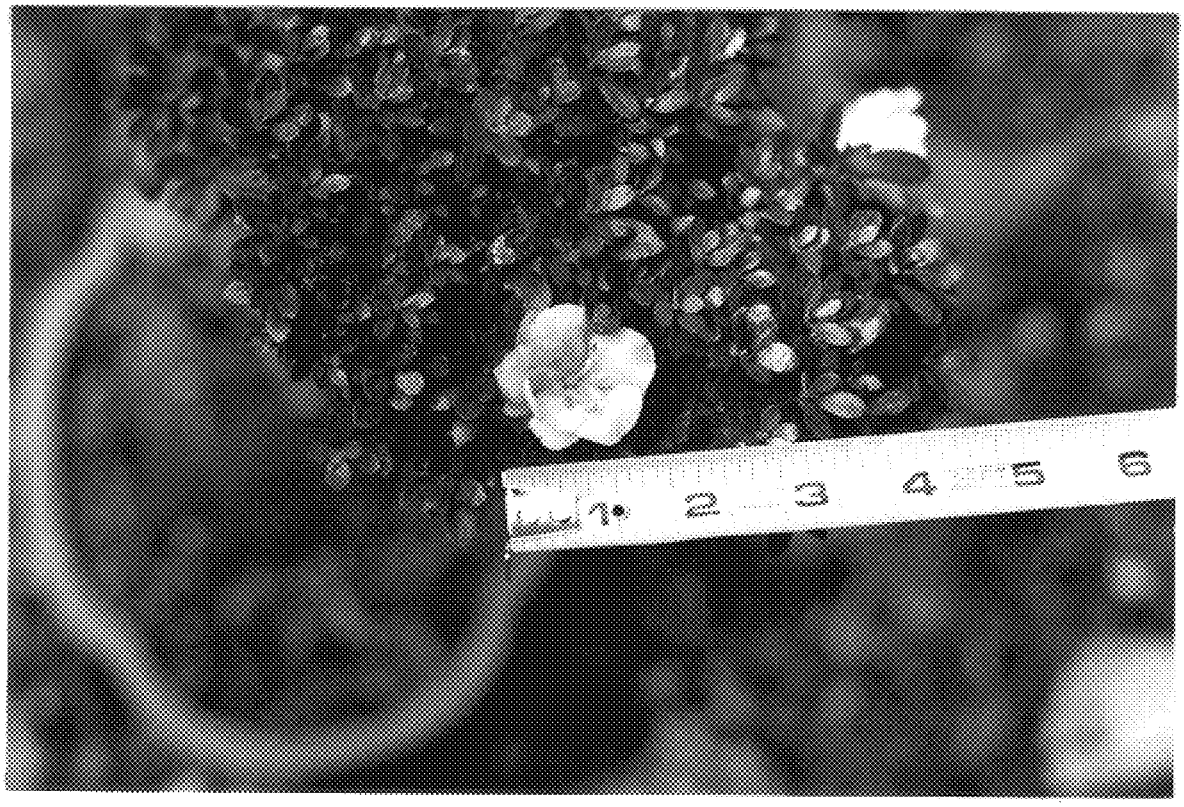
FIG. 1 is a photograph that shows flower size.
Figure 2:
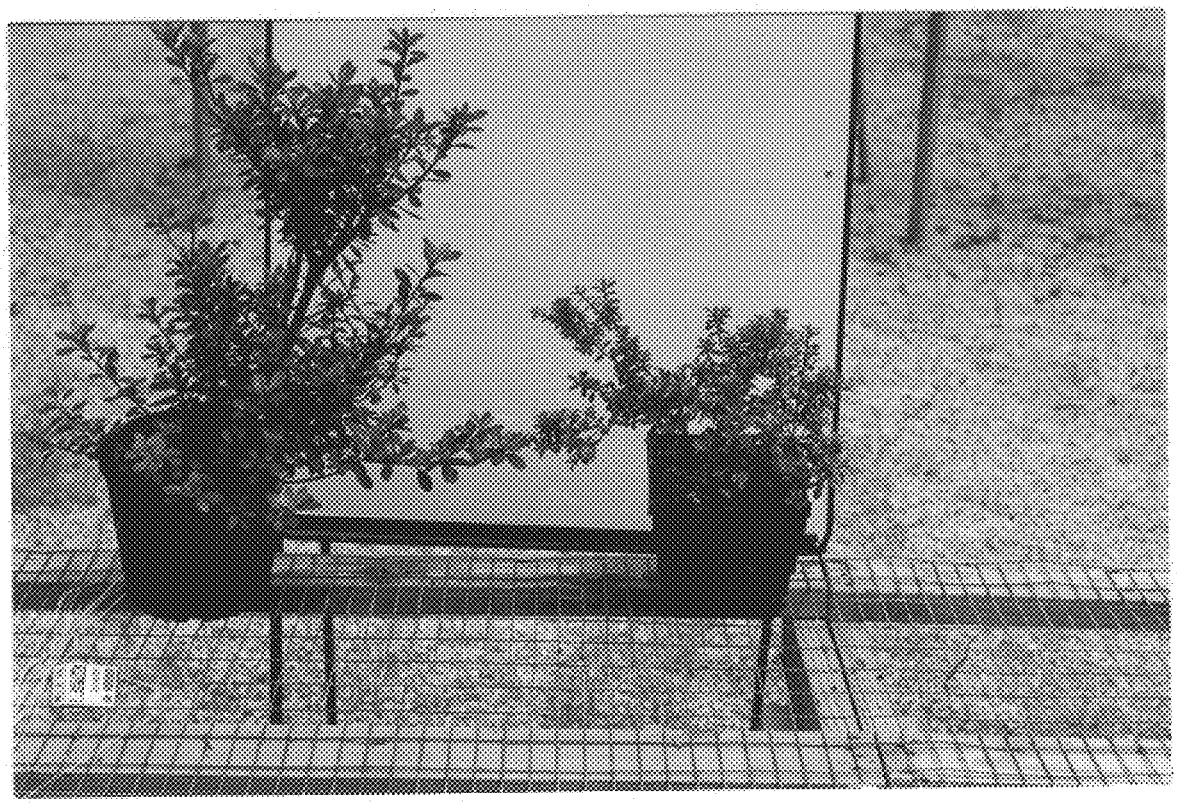
FIG. 2 is a photograph that shows the overall appearance of both the new variety (on the right) and the parent (on the left) in a side by side view for comparison.
Figure 3:
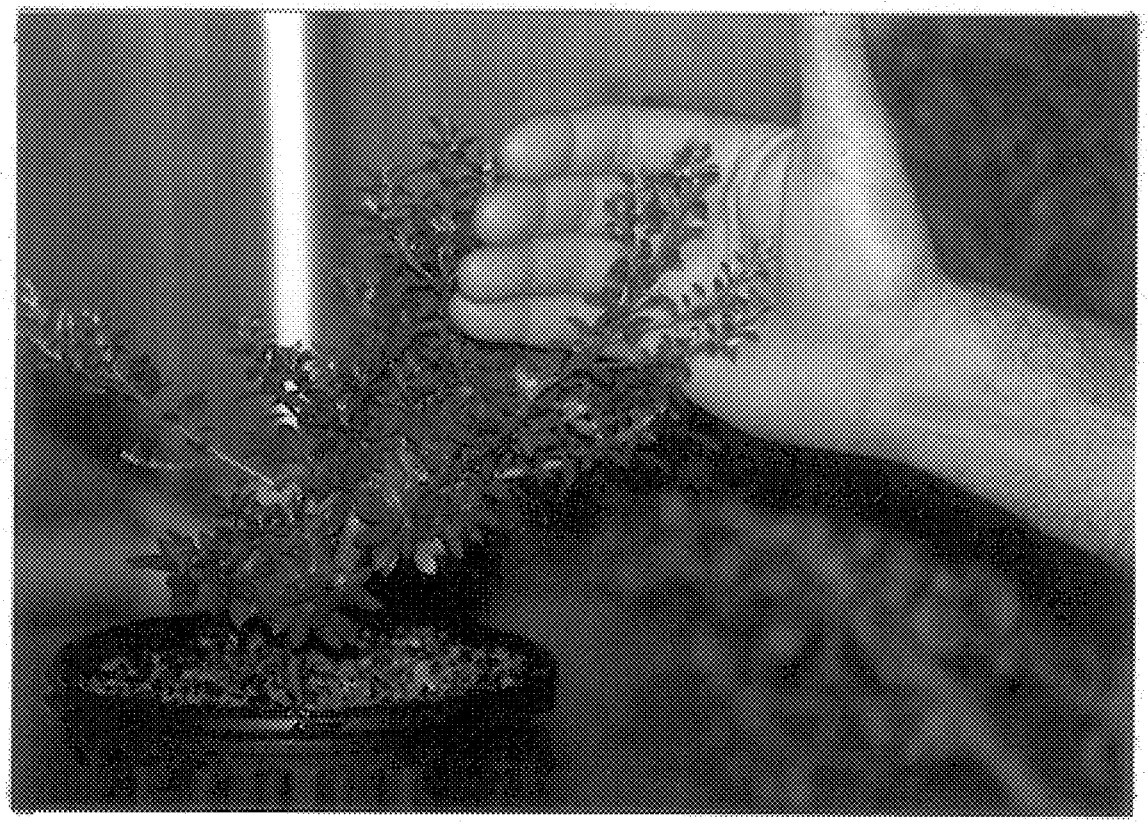
FIG. 3 is a photograph showing a close up of the unique branching.

Actual leaf and inflorescence colors may differ from leaf and inflorescence colors in the photographs due to light reflectance.

DESCRIPTION OF THE PLANT

The descriptive matter which follows pertains to the new variety 'Sweet Lorraine' when grown in the vicinity of Covington, La., under full sun to partial shade and is believed to apply when the new variety is grown under similar conditions of soil and climate elsewhere, the soil type being 50% decomposed pine bark and 50% haydite (fired clay). Color determinations are based on the Munsell Book of Color.

GENERAL CHARACTERISTICS

The plant is a low and spreading shrub with miniature leaves and demonstrates the ability to spontaneously produce foliage buds without pruning, hence branches heavily and is more vigorous than the parent. The new plant flowers profusely in May and June and is an ideal plant for the bonsai market as well as other commercial markets.

Origin: Naturally occuring branch sport.
Parentage: Azalea plant named 'Wakaebisu' (unpatented).

Growth: Compact, dense, and vigorous.

Size: The ultimate size is unknown, as no plant has yet reached full maturity although a 3 year old plant grown in a 3 gallon container reached 27 inchess in height with a width of 23 inches and a trunk diameter of 1½ inches.

Disease Resistance: Typical of the species, as determined by comparison with other azalea varieties grown under the same cultural conditions at Covington, La.

Foliage:

*Arrangement.*—Alternate.

*Type.*—Evergreen.

*Leaves.*—Single.

*Color.*—Immature — Upper surface 7.5 GY 6/4. Under surface 5 GY 6/6. Mature — Upper surface 7.5 GY 4/4. Under surface 7.5 GY 6/4.

*Size.*—Average length — 5/16 to ½ inch. Average width — 3/16 to 5/16 inch.

*Shape.*—Elliptic to Obovate.

*Apex.*—Acute to acuminate.

*Base.*—Cuneate to attenuate.

*Margin.*—Entire.

*Texture.*—Coarse and glossy.

*Bud.*—Color — 5 GY 4/6.

*Petiole.*—Length — 1/16 to ⅛ inch Color — 2.5 GY 6/6.

*Stem.*—Color (Mature) — 2.5 GY 6/8 (Immature) — 2.5 GY 5/8 with hairs 10 Y 8/8.

Flower:

*Quantity of bloom.*—Abundant, both outdoors and in greenhouse.

*Blooming habit.*—Profuse, May and June.

*Size.*—Average 1½ to 2½ inch blooms.

*Type.*—Hose in hose with an open rounded form.

*Petalage.*—Number — 5. Color — Upper surface 2.5 R 7/10 with dots in throat 1.25 R 5/12. Under surface 2.5 R 7/10.

*Bud.*—Length — ⅜ to ½ inch. Width — ¼ to 5/16 inch. Color — 2.5 R 7/8.

*Calyx.*—Color — 2.5 R 7/8.

*Pedicel.*—Color — 2.5 GY 8/4.

*Peduncle.*—Color — 2.5 GY 8/4.

Reproductive organs:

*Stamen.*—Color — 2.5 R 8/4.

*Pistil.*—Color — 10 Rp 7/8.

*Stigma.*—Color — 10Y 8.5/8.

*Style.*—Color — 2.5 R 8/6.

I claim:

1. A new and distinct variety of Azalea plant named 'Sweet Lorraine' as herein illustrated and described.

* * * * *